US007452702B2

(12) United States Patent
Lee (10) Patent No.: US 7,452,702 B2
(45) Date of Patent: Nov. 18, 2008

(54) METHOD FOR PRODUCING FATS OR OILS

(75) Inventor: Immok Lee, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 735 days.

(21) Appl. No.: 10/875,532

(22) Filed: Jun. 25, 2004

(65) Prior Publication Data

US 2005/0014237 A1 Jan. 20, 2005

Related U.S. Application Data

(60) Provisional application No. 60/487,261, filed on Jul. 16, 2003.

(51) Int. Cl.
C12P 7/64 (2006.01)
C11B 1/00 (2006.01)
(52) U.S. Cl. .................. 435/134; 435/800; 435/962; 554/2; 554/8; 554/29; 554/175
(58) Field of Classification Search ................ 435/134, 435/800, 962; 554/2, 8, 29, 175
See application file for complete search history.

(56) References Cited

U.S. PATENT DOCUMENTS

| 2,206,168 | A | 7/1940 | Edeler et al. |
|---|---|---|---|
| 2,626,952 | A | 1/1953 | Lange et al. |
| 3,360,533 | A | 12/1967 | Wootton et al. |
| 3,634,473 | A | 1/1972 | Harwood |
| 3,845,087 | A | 10/1974 | de Groot |
| 4,154,749 | A | 5/1979 | Krawack |
| 4,275,081 | A | 6/1981 | Coleman et al. |
| 4,276,322 | A | 6/1981 | Padley et al. |
| 4,454,329 | A | 6/1984 | Takagi et al. |
| 4,656,045 | A | 4/1987 | Bodor et al. |
| 4,735,900 | A | 4/1988 | Urata et al. |
| 4,770,819 | A | 9/1988 | Zinnen |
| 4,797,233 | A | 1/1989 | Zinnen |
| 4,798,793 | A | 1/1989 | Eigtved |
| 4,863,860 | A | 9/1989 | Halling et al. |
| 4,873,109 | A | 10/1989 | Tanaka et al. |
| 4,880,652 | A | 11/1989 | Regutti |
| 4,883,684 | A | 11/1989 | Yang |
| 4,940,845 | A | 7/1990 | Hirota et al. |
| 4,966,734 | A | 10/1990 | Hoercher et al. |
| 5,102,582 | A | 4/1992 | Zinnen |
| 5,108,916 | A | 4/1992 | Cobbs et al. |
| 5,116,745 | A | 5/1992 | Mazur et al. |
| 5,124,166 | A | 6/1992 | Jacklin et al. |
| 5,128,251 | A | 7/1992 | Yokomichi et al. |
| 5,137,660 | A | 8/1992 | Mazur et al. |
| 5,142,072 | A | 8/1992 | Stipp et al. |
| 5,149,642 | A | 9/1992 | Mazur et al. |
| 5,166,064 | A | 11/1992 | Usui et al. |
| 5,183,750 | A | 2/1993 | Nishide et al. |
| 5,190,868 | A | 3/1993 | Kokusho et al. |
| 5,204,251 | A | 4/1993 | Kyotani et al. |

| 5,209,826 | A | | 5/1993 | Ozaki et al. |
|---|---|---|---|---|
| 5,219,733 | A | | 6/1993 | Myojo et al. |
| 5,219,744 | A | | 6/1993 | Kurashige et al. |
| 5,270,188 | A | | 12/1993 | Yamaguchi et al. |
| 5,273,898 | A | * | 12/1993 | Ishii ........................... 435/134 |
| 5,288,619 | A | | 2/1994 | Brown et al. |
| 5,292,649 | A | | 3/1994 | Kosugi et al. |
| 5,399,728 | A | | 3/1995 | Cooper |
| 5,461,170 | A | | 10/1995 | Miyamoto et al. |
| 5,508,182 | A | | 4/1996 | Schneider et al. |
| 5,543,110 | A | | 8/1996 | Starr et al. |
| 5,578,090 | A | | 11/1996 | Bradin |
| 5,650,157 | A | * | 7/1997 | Bockow ..................... 424/401 |
| 5,658,768 | A | | 8/1997 | Quinlan |
| 5,670,669 | A | | 9/1997 | Hunt |
| 5,713,965 | A | | 2/1998 | Foglia et al. |
| 5,773,266 | A | | 6/1998 | Bosley et al. |
| 5,959,128 | A | | 9/1999 | Kolstad et al. |
| 5,981,781 | A | | 11/1999 | Knowlton |
| 5,994,286 | A | | 11/1999 | Desai et al. |
| 6,004,611 | A | | 12/1999 | Gotoh et al. |
| 6,011,131 | A | | 1/2000 | Sato et al. |
| 6,160,143 | A | | 12/2000 | Alasti |
| 6,162,483 | A | | 12/2000 | Wester |
| 6,172,248 | B1 | | 1/2001 | Copeland et al. |
| 6,258,575 | B1 | | 7/2001 | Shimizu et al. |
| 6,281,373 | B1 | | 8/2001 | Sato et al. |
| 6,361,980 | B2 | | 3/2002 | Sugiura et al. |
| 6,398,707 | B1 | | 6/2002 | Wu et al. |
| 6,407,269 | B2 | | 6/2002 | Kaita et al. |
| 6,511,690 | B1 | | 1/2003 | Tysinger et al. |
| 6,660,491 | B2 | | 12/2003 | Norinobu et al. |
| 2003/0054509 | A1 | | 3/2003 | Lee et al. |
| 2003/0104109 | A1 | | 6/2003 | Jacobs et al. |
| 2005/0019316 | A1 | | 1/2005 | Ten Brink et al. |

FOREIGN PATENT DOCUMENTS

EP 0 010 333 A1 4/1980

(Continued)

OTHER PUBLICATIONS

"AOCS Official Method Cc 18-80, Dropping Point," in *Official Methods and Recommended Practices of the AOCS, 5th Edition*, Firestone, D., et. al., eds., The American Oil Chemists' Society, Champaign, IL, 2 pages (1998).

(Continued)

*Primary Examiner*—Herbert J. Lilling
(74) *Attorney, Agent, or Firm*—Sterne, Kessler, Goldstein & Fox P.L.L.C.

(57) ABSTRACT

The present invention is directed to improving productivity of an enzymatic method for making esterified, transesterified or interesterified products. Specifically, a method that can greatly improve the productivity of enzymatic transesterification or esterification by deodorization alone, or by deodorization and purification of the initial substrate to extend the useful life of the enzyme is disclosed.

40 Claims, 1 Drawing Sheet

FOREIGN PATENT DOCUMENTS

| | | |
|---|---|---|
| EP | 0 188 122 A1 | 7/1986 |
| EP | 0 307 154 B1 | 3/1989 |
| EP | 0 378 893 B1 | 7/1990 |
| EP | 1 004 662 A2 | 5/2000 |
| EP | 1 094 116 A1 | 4/2001 |
| EP | 1 111 064 A1 | 6/2001 |
| GB | 617078 | 2/1949 |
| JP | 2-203789 | 8/1990 |
| JP | 2-203790 | 8/1990 |
| JP | 8-140689 | 6/1996 |
| JP | 11-103884 | 4/1999 |
| JP | 2003-310290 | 11/2003 |
| WO | WO 99/09119 A1 | 2/1999 |

OTHER PUBLICATIONS

"AOCS Official Method Cd 16b-93, Solid Fat Content (SFC) by Low-Resolution Nuclear Magnetic Resonance—The Direct Method," in *Official Methods and Recommended Practices of the AOCS, 5th Edition*, The American Oil Chemists' Society, Champaign, IL, 10 pages (1999).

"AOCS Official Method Cd 8-53, Peroxide Value Acetic Acid-Chloroform Method," in *Official Methods and Recommended Practices of the AOCS, 5th Edition*, Firestone, D., et. al., eds., The American Oil Chemists' Society, Champaign, IL, 2 pages (1997).

Brekke, O.L., "Deodorization", In *Handbook of Soy Oil Processing and Utilization*, Erickson, D.R., et. al. eds., pp. 155-191, American Soybean Association and the American Oil Chemists' Society, St. Louis, MO and Champaign, IL (1991).

Buzás, I. and Kurucz, É., "Study of the Thermooxidative Behavior of Edible Oils by Thermal Analysis," *J. Am. Oil Chem. Soc.* 56: 685-688, American Oil Chemists' Society (1979).

*Food Lipids: Chemistry, Nutrition, and Biotechnology, Second Edition, Revised and Expanded*, Akoh, C.C., and Min, D.B. eds., Marcel Dekker, Inc., New York, NY, pp. 865-869 (Apr. 2002).

Gavin, A.M., "Deodorization and Finished Oil Handling," *J. Am. Oil. Chem. Soc.* 58: 175-184, American Oil Chemists' Society (1981).

Goderis, H.L., et. al., "Lipase-Catalyzed Ester Exchange Reactions in Organic Media with Controlled Humidity," *Biotech. Bioeng.* 30:258-266, John Wiley & Sons, Inc. (1987).

Gray, J.I., "Measurement of Lipid Oxidation: A Review," *J. Am. Oil. Chem. Soc.* 55: 539-546, American Oil Chemists' Society (1978).

Hui, Y.H., ed., "5.6 Deodorization," in *Baileys' Industrial Oil and Fat Products, Edible Oil and Fat Products: Oils and Oil Seeds, 5th edition*, vol. 2, Hui, Y.H., ed., John Wiley & Sons, Inc., New York, NY, pp. 537-540 (1991).

Hui, Y.H., ed., "Deodorization," Chapter 6 in *Baileys' Industrial Oil and Fat Products, Edible Oil and Fat Products: Processing Technology, 5th edition*, vol. 4, Hui, Y.H., ed., John Wiley & Sons, Inc., New York, NY, pp. 339-390 (1996).

Hung, S.S.O. and Slinger, S.J., "Studies of Chemical Methods for Assessing Oxidative Quality and Storage Stability of Feeding Oils," *J. Am. Oil. Chem. Soc.* 58:785-788, American Oil Chemists' Society (1981).

Lau, F.Y., et. al., "Effect of Randomization on the Oxidation of Corn Oil," *J. Am. Oil Chem. Soc.* 59:407-411, American Oil Chemists' Society (1982).

Linfield, W.M., et. al., "Enzymatic Fat Hydrolysis and Synthesis," *J. Am. Oil Chem. Soc.* 61:191-195, American Oil Chemists' Society (1984).

Macrae, A.R., "Lipase-Catalyzed Interesterification of Oils and Fats," *J. Am. Oil Chem. Soc.* 60:291-294, American Oil Chemists' Society (1983).

Macrae, A.R., "Enzyme-catalysed modification of oils and fats," *Phil. Trans. R. Soc. Lond. B*.310:227-233, The Royal Society (1985).

Merolli, A., et. al., "Medium-chain lipids: new sources, uses," *INFORM* 8:597-603, American Oil Chemists' Society Press (1997).

Miller, C., et. al., "Characteristics of an Immobilized Lipase for the Commercial Synthesis of Esters," *J. Am. Oil. Chem. Soc.* 65:927-931, American Oil Chemists' Society (1988).

Patterson, J.D.E., et. al., "Synthesis of Glycerides and Esters by Fungal Cell-Bound Enzymes in Continuous Reactor Systems," *Biotechnol. Lett.* 1:211-216, Kew and Science and Technology Letters (1979).

Pederson, L.S. and Nielson, P.M., "Enzymatic interesterification," in *Bulk Fat Manual:Enzymatic interesterification in bulk fat modification*, Novozymes, Denmark (May 2002).

Rousseau, D. and Marangoni, A.G., "Chemical Interesterification of Food Lipids: Theory and Practice," in *Food Lipids: Chemistry, Nutrition, and Biotechnology, Second Edition, Revised and Expanded*, Akoh, C.C., and Min, D.B., eds., Marcel Dekker, Inc., New York, NY, pp. 301-304 (Apr. 2002).

Snyder, J.M., et. al., "Headspace Volatile Analysis to Evaluate Oxidative and Thermal Stability of Soybean Oil. Effect of Hydrogenation and Additives," *J. Am. Oil Chem. Soc.* 63: 1055-1058, American Oil Chemists' Society (1986).

Sonnet, P.E., "Kinetic Resolutions of Aliphatic Alcohols with a Fungal Lipase from *Mucor miehei*," *J. Org. Chem.* 52:3477-3479, American Chemcial Society (1987).

Tsujisaka, Y., et. al., "Glyceride Synthesis by Four Kinds of Microbial Lipase," *Biochim. Biophys. Acta* 489:415-422, Elsevier/North-Holland Biomedical Press (1977).

Zhang, H., et. al., "Production of Margarine Fats by Enzymatic Interesterification with Silica-Granulated *Thermomyces lanuginosa* Lipase in a Large-Scale Study," *J. Am. Oil Chem. Soc.* 78:57-64, American Oil Chemists' Society Press (2001).

Unverified partial translation of JP 2-203789 (Document AL2).
Unverified translation of JP 2-203790 (Document AM2).
Unverified translation of JP 8-140689 (Document AN2).
Unverified partial translation of JP 11-103884 (Document AP2).
Unverified partial translation of JP 2003-310290 (Document AO3).
Unverified translation of JP 8-140689 (Document AN2), Jun. 1996.
Unverified partial translation of JP 11-103884 (Document AP2), Apr. 1999.
Unverified partial translation of JP 2003-310290 (Document AO3), Apr. 1999.
Unverified partial translation of JP 2-203789 (Document AL2), Aug. 1990.
Unverified translation of JP 2-203790 (Document AM2), Aug. 1990.

* cited by examiner

FIG. 1

METHOD FOR PRODUCING FATS OR OILS

BACKGROUND OF THE INVENTION

1. Field of the Invention

The invention relates to methods for producing fats and oils. Specifically, the invention pertains to prolonging the enzymatic activity of an enzyme used for transesterification or esterification of a substrate for the production of fats and oils by deodorization of the substrate prior to transesterification or esterification. The invention also relates to using deodorization in tandem with a purification medium.

2. Related Art

Fats and oils are composed principally of triglycerides made up of a glycerol moiety in which the hydroxyl groups are esterified with carboxylic acids. Whereas solid fats tend to be formed by triglycerides having saturated fatty acids, triglycerides with unsaturated fatty acids tend to be liquid (oils) at room temperature. Monoglycerides and diglycerides, having respectively one fatty acid ester and two alcoholic groups or two fatty acid esters and one alcoholic group, are also found in fats and oils to a lesser extent than triglycerides.

Many fats and oils are readily obtained from processing plant or animal matter. However, some fats and oils are obtained via well-known chemical or enzymatic transesterification or esterification processes. By these processes, one or more of the fatty acid groups on a glyceride is transferred, hydrolyzed or replaced with a different fatty acid group. Chemical methods require harsh alkaline conditions, high temperatures and generate wasteful by-products. The discolored fats and oils produced need to be neutralized, washed and centrifuged to remove catalysts, and ultimately bleached. In addition to these problems, chemical transesterification or chemical esterification is non-specific in the glyceride position or type of fatty acid group transferred, hydrolyzed or replaced. It is thus very difficult or impossible to produce specific fats or oils via large scale chemical catalytic processes. In contrast, enzymatic methods of transesterification or esterification are simpler, cleaner, environmentally friendly and are highly specific with respect to modifying glyceride fatty acid groups.

One family of enzymes capable of affecting this transesterification or esterification in glycerides are known as lipases. Lipases are obtained from prokaryotic or eukaryotic microorganisms and typically fall into one of three categories (Macrae, A. R., J.A.O.C.S.60:243A-246A (1983)).

The first category includes nonspecific lipases capable of releasing or binding any fatty acid group from or to any glyceride position. Such lipases have been obtained from *Candida cylindracae, Corynebacterium acnes* and *Staphylococcus aureus* (Macrae, 1983; U.S. Pat. No. 5,128,251). The second category of lipases only adds or removes specific fatty acid groups to or from specific glycerides. Thus, these lipases are useful in producing or modifying specific glycerides. Such lipases have been obtained from *Geotrichum candidium* and *Rhizopus, Aspergillus*, and *Mucor* genera (Macrae, 1983; U.S. Pat. No. 5,128,251). The last category of lipases catalyze the removal or addition of fatty acid groups from the glyceride carbons on the end in the 1- and 3-positions. Such lipases have been obtained from *Thermomyces lanuginosa, Rhizomucor miehei, Aspergillus niger, Mucor javanicus, Rhizopus delemar*, and *Rhizopus arrhizus* (Macrae, 1983).

The last category of enzymes have wide applicability. For example, cocoa butter consists primarily (about 70-80% by weight) of saturated-oleic-saturated (SOS) triglycerides (European published patent application no. EP 0188122 A1). It is this triglyceride composition which provides the unique characteristics by which chocolate products hold their shape at room temperature but melt slightly below human body temperature (see U.S. Pat. No. 4,276,322). These SOS triglycerides include 1,3-dipalmitoyl-2-monooleine (POP), 1(3)-palmitoyl-3(1)-stearoyl-2-monooleine (POSt) and 1,3-distearoyl-2-monooleine (StOSt). Thus, oleic acid-rich glycerides with an oleic ester group in the middle position can be incubated with palmitic and stearic acid in the presence of a 1,3-specific lipase to produce POP, POSt and StOSt, i.e., cocoa butter substitutes (U.S. Pat. No. 4,276,322). The production of cocoa butter substitutes alleviates food manufacturers from widely fluctuating cocoa butter supply and cost. 1,3-specific lipases also are useful in the manufacture of specialty 1,3-diglycerides, as described in U.S. Pat. No. 6,004,611.

Despite these benefits, enzymatic transesterification or esterification is a costly process because of the expense in providing a large amount of purified lipase. Moreover, the enzymatic activity of lipase decays with time and with exposure to large amounts of fats or oils. The present invention reduces these problems by providing an enzymatic method for producing fats or oils by which the enzymatic activity of lipase is prolonged.

SUMMARY OF THE INVENTION

The present invention relates to a method of making an esterified, transesterified or interesterified product comprising:
(a) forming an initial substrate comprising one or more fats or oils;
(b) deodorizing the initial substrate thereby reducing the constituents which cause or arise from fat or oil degradation and thereby producing a deodorized substrate;
(c) contacting the deodorized substrate with an enzyme thereby making the esterified, transesterified or interesterified product;

wherein the half-life of the enzyme is prolonged.

DETAILED DESCRIPTION OF THE PREFERRED EMBODIMENT

For purposes herein, the term "initial substrate" includes refined or unrefined, bleached or unbleached and/or deodorized or non-deodorized fats or oils. The fats or oils can comprise a single fat or oil or combinations of various fats or oils. The term "deodorized substrate" refers to a substrate which has undergone at least one deodorization process. The term "purification media-processed substrate" refers to a substrate which has contacted one or more purification media at least once. Prior to its contact with enzyme, a deodorized substrate or a purification media-processed substrate can be mixed with additional components including esters, free fatty acids or alcohols. Prior to its contact with purification media, a deodorized substrate can be mixed with additional components including esters, free fatty acids or alcohols. Preferably, these esters, free fatty acids or alcohols which are added to the deodorized substrate or purification media-processed substrate are not themselves subjected to the deodorization process. However, these additional components can optionally contact purification media. Except where reference is explicitly or implicitly made to a substrate which has not been deodorized, the term "substrate" includes deodorized substrate or purification media-processed substrate, either of which optionally have one or more of the aforementioned additional components.

The terms "product" and "esterified, transesterified or interesterified product" are used interchangeably and include esterified, transesterified or interesterified fats, oils, triglycerides, diglycerides, monoglycerides, mono- or polyhydroxyl alcohols, or esters of mono- or polyhydroxyl alcohols produced via the enzymatic transesterification or esterification process. Product has come into contact at least once with an enzyme capable of causing esterification, transesterification or interesterification. Product can be a fluid or solid at room temperature. Product is increased in its proportional content of esterified, transesterified or interesterified fats, oils, triglycerides, diglycerides, monoglycerides, mono- or polyhydroxyl alcohols, or esters of mono- or polyhydroxyl alcohols as a result of their having contacted the transesterification or esterification enzyme. Esterified, transesterified or interesterified product is to be distinguished from the contents of initial substrate, deodorized substrate, or purification-media processed substrate in that product has undergone additional enzymatic transesterification or esterification reaction. The present invention contemplates use of any combination of the deodorization, purification and transesterification or esterification processes for the production of esterified, transesterified or interesterified fats, oils, triglycerides, diglycerides, monoglycerides, mono- or polyhydroxyl alcohols, or esters of mono- or polyhydroxyl alcohols.

The term "enzyme" as used in the method of the present invention includes lipases, as discussed herein, or any other enzyme capable of causing esterification, transesterification or interesterification of substrate.

According to the present invention, a substrate can be recycled (i.e., deodorized, contact purification media, esterified, transesterified or interesterified more than once). Hence, the skilled artisan would recognize that "initial substrate" includes i) substrates that have never been deodorized, ii) substrates that have been deodorized one or more times, iii) substrates that have never contacted purification media, iv) substrates that have contacted purification media one or more times, v) substrates that have never been esterified, transesterified or interesterified, and vi) substrates that have been esterified, transesterified or interesterified one or more times.

Glycerides useful in the present invention include molecules given by the chemical formula $CH_2RCHR'CH_2R''$ wherein R, R' and R" are alcohols (OH) or fatty acid groups given by —OC(=O)R''', wherein R''' is a saturated, unsaturated or polyunsaturated, straight or branched carbon chain with or without substituents. R, R', R" and the fatty acid groups on a given glyceride can be the same or different. The acid groups R, R' and R" can be obtained from any of the free fatty acids described herein. Glycerides for the present invention include triglycerides in which R, R' and R" are all fatty acid groups, diglycerides in which two of R, R' and R" are fatty acid groups and one alcohol functionality is present; monoglycerides in which one of R, R' and R" is a fatty acid group and two alcohol functionalities are present; and glycerol in which each of R, R' and R" is an alcohol group. Glycerides useful as starting materials of the invention include natural, processed, refined and synthetic fats and oils. Examples of refined fats and oils are described herein and in Stauffer, C.,*Fats and Oils*, Eagan Press, St. Paul, Minn. Examples of processed fats and oils are hydrogenated and fractionated fats and oils.

The terms "fatty acid groups" or "acid groups" both refer to chemical groups given by —OC(=O)R'''. Such "fatty acid groups" or "acid groups" are connected to the remainder of the glyceride via a covalent bond to the oxygen atom that is singly bound to the carbonyl carbon. In contrast, the terms "fatty acid" or "free fatty acid" both refer to HOC(=O)R''' and are not covalently bound to a glyceride. In "fatty acid groups," "acid groups," "free fatty acids," and "fatty acids," R''' is a saturated, unsaturated or polyunsaturated, straight or branched carbon chain with or without substituents, as discussed herein. The skilled artisan will recognize that R''' of the "free fatty acids" or "fatty acids" (i.e., HOC(=O)R''') described herein are useful as R''' in the "fatty acid groups" or "acid groups" attached to the glycerides or to other esters used as substrates in the present invention. That is, a substrate of the present invention may comprise fats, oils or other esters having fatty acid groups formed from the free fatty acids or fatty acids discussed herein.

"Esterification" or "transesterification" are the processes by which an acid group is added, hydrolyzed, repositioned or replaced on one or more components of the substrate. The acid group can be derived from a fat or oil which is part of the initial substrate, or from a free fatty acid or ester that has been added to the deodorized substrate or purification media-processed substrate.

The term "esterification" includes the process in which R, R' or R" on a glyceride is converted from an alcoholic group (OH) to a fatty acid group given by —OC(=O)R'''. The fatty acid group which replaces the alcoholic group can come from the same or different glyceride, or from a free fatty acid or ester that has been added to the deodorized substrate or the purification media-processed substrate. The present invention also contemplates esterification of alcohols which have been added to the deodorized substrate or the purification media-processed substrate. For example, an alcohol so added may be esterified by an added free fatty acid or by a fatty acid group present on a glyceride which was a component of the initial substrate. A non-limiting example of esterification includes reaction of a free fatty acid with an alcohol.

The term "transesterification" includes the process in which R, R' or R" on a glyceride is a first fatty acid group given by —OC(=O)R''', and the first fatty acid group is replaced by a second, different fatty acid group. The second fatty acid group which replaces the first fatty acid group can come from the same or different fat or oil present in the initial substrate. The second fatty acid can also come from a free fatty acid or ester added to the deodorized substrate or the purification media-processed substrate. The present invention also contemplates transesterification or interesterification of esterified alcohols or other esters which have been added to the deodorized substrate or the purification media-processed substrate. For example, an alcohol so added may be transesterified or interesterified by an added free fatty acid, by a fatty acid group on an added ester, or by a fatty acid group present on a glyceride which was a component of the initial substrate. A non-limiting example of transesterification includes reaction of a fat or oil with an alcohol (e.g., methanol) or with an ester.

The term "interesterification" includes the processes acidolysis, alcoholysis, glycerolysis, and transesterification. Examples of these processes are described herein, and in Fousseau, D. and Marangoni, A. G., "Chemical Interesterification of Food Lipids: Theory and Practice," in *Food Lipids Chemistry, Nutrition, and Biotechnology, Second Edition*,

*Revised and Expanded*, Akoh, C. C. and Min, D. B. eds., Marcel Dekker, Inc., New York, N.Y., Chapter 10. Acidolysis includes the reaction of a fatty acid with a triacylglycerol; alcoholoysis includes the reaction of an alcohol with a triacylglycerol; and glycerolyis includes alcoholysis reactions in which the alcohol is glycerol. A non-limiting example of nteresterification or transesterification includes reactions of different triglycerides resulting in randomization of the fatty acid group.

Esterification also includes processes pertaining to the manufacture of biodiesel, such as discussed in U.S. Pat. Nos. 5,578,090; 5,713,965; and 6,398,707. The term "biodiesel" includes lower alkyl esters of fatty acid groups found on animal or vegetable glycerides. Lower alkyl esters include methyl ester, ethyl ester, n-propyl ester, and isopropyl ester. In the production of biodiesel, the initial substrate comprises fats or oils and is deodorized as described herein. One or more lower alcohols (e.g., methanol, ethanol, n-propanol and isopropanol) are added to this substrate and the mixture then comes into contact with enzyme. The enzyme causes the alcohols to be esterified with the fatty acid groups which is part of the fat or oil glycerides. For example, R, R' or R" on a glyceride is a fatty acid group given by —OC(=O)R'". Upon esterification of methanol, the biodiesel product is $CH_3OC(=O)R'''$. Biodiesel products also include esterification of lower alcohols with free fatty acids or other esters which are added to the deodorized substrate.

An esterified, transesterified or interesterified product has respectively undergone the esterification, transesterification or interesterification process. The present invention relates to enzymes capable of affecting the esterification, transesterification or interesterification process for fats, oils, triglycerides, diglycerides, monoglycerides, free fatty acids, mono- or polyhydroxyl alcohols, or esters of mono- or polyhydroxyl alcohols.

As used herein, the "half-life" of an enzyme is the time in which the enzymatic activity of an enzyme sample is decreased by half. If, for example, an enzyme sample decreases its relative activity from 100 to 50 in 10 minutes, then the half life of the enzyme sample is 10 minutes. If the half-life of this sample is constant, then the relative activity will be reduced from 100 to 25 in 20 minutes (two half lives), the relative activity will be reduced from 100 to 12.5 in 30 minutes (three half lives), the relative activity will be reduced from 100 to 6.25 in 40 minutes (four half lives), etc. As used herein, the expression "half-life of an enzyme" means the half-life of an enzymatic sample.

A "prolonged" half-life refers to an increased "half-life". Prolonging the half-life of an enzyme results in increasing the half life of an enzyme by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 210%, 220%, 230%, 240%, 250%, 260%, 270%, 280%, 290%, 300%, 320%, 340%, 360%, 380%, 400%, 420%, 440%, 460%, 480%, 500% or more as compared to the half-life of an enzyme used in an esterified, transesterified or interesterified fat or oil producing process which does not employ deodorization and/or a purification medium.

Non-limiting examples of "constituents which cause or arise from fat or oil degradation" include oxidative or oxidating species, reactive oxygen species, fat or oil oxidation products, peroxides, ozone ($O_3$), $O_2$, superoxide, free fatty acids, volatile organic compounds, free radicals, trace metals, and natural prooxidants such as chlorophyll. Such constituents also include other characterized or uncharacterized compounds recognized by the skilled artisan to cause or arise from fat or oil degradation. Such constituents can arise from oxidation pathways, or from other pathways recognized by the skilled artisan to result in fat or oil degradation. "Reducing" the constituents which cause or arise from fat or oil degradation in a substrate sample refers to lowering the concentration, percentage or types of such constituents in the sample.

A variety of factors lead to the degradation of fats and oils. This has, in part, been identified as due to fat or oil lipids becoming rancid as a consequence of oxidation. See Gray, J. I., "Measurement of Lipid Oxidation: A Review," J.A.O.C.S. 55: 539-546 (1978). Fat or oil oxidation can be caused by a variety of factors including exposure to oxygen, air, heat, light, or prooxidant metals; or simply by the lapse of time. See Gavin, A. M. "Deodorization and Finished Oil Handling," J.A.O.C.S. 58: 175-184 (1981). Over time, deodorized oil can take on the characteristics of non-deodorized oil. The presence of minor impurities including oxidative species that initiate self-propagated radical reaction pathways, or other reactive oxygen species (such as peroxides, ozone, superoxide, etc.) also affect fat or oil oxidation. However, the processes by which fats and oils become degraded are not completely understood.

A variety of chemical assays have been developed to help quantitatively assess constituents which cause or arise from fat or oil degradation. These assays can evaluate the relative oxidation level in fat or oil by quantitating constituents which cause or arise from fat or oil degradation present in a given fat or oil sample. For example, a fat or oil sample's peroxide value (PV) can be evaluated using the Stamm method (see Lau, F.Y. et al., "Effect of Randomization on the Oxidation of Corn Oil," J.A.O.C.S. 59:407-411 (1982)) or via AOCS Official Method Cd 8-53. Other methods for evaluating a sample's relative oxidation level include assessing the anisidine value (AV), thiobarbituric acid number (TBA), carbonyl value (CV) and percent free fatty acids (FFA). See Hung, S. S. O. and Slinger, S. J. "Studies of Chemical Methods for Assessing Oxidative Quality and Storage Stability of Feeding Oils," J.A.O.C.S. 58: 785-788 (1981). Oxidative changes of fats or oils can also be monitored using thermogravimetry (TG) and derivative thermogravimetry (DTG) curves, or differential thermal analysis (DTA). See Buzás, I. and Kurucz, É. "Study of the Thermooxidative Behavior of Edible Oils by Thermal Analysis," J.A.O.C.S. 56: 685-688 (1979). Oxidation levels can also be measured by monitoring changes in a fat or oil sample's total or individual volatile components. See Snyder, J. M. et al., "Headspace Volatile Analysis to Evaluate Oxidative and Thermal Stability of Soybean Oil. Effect of Hydrogenation and Additives," J.A.O.C.S. 63: 1055-1058 (1986). The skilled artisan will be familiar with other manners by which to assess a fat or oil sample's relative oxidation.

Deodorization can remove some of the constituents which are quantitated by the above described assays. Typically, deodorization is the last step of the conventional edible oil refining process performed to improve the taste, odor, color and stability of oils by removal of these undesirable substances. Deodorization is principally a steam distillation, during which substances with greater volatility are removed by high temperature under vacuum. Introduction of steam, or an inert gas, into the deodorizer greatly increases the volatilization efficiency. Various substances removed by deodorization include free fatty acids and various flavor and odor compounds either present originally or generated by oxidation of fats and oils. Also removed are the substances formed by the heat decomposition of peroxides and pigments.

Examples of deodorization processes include the deodorization techniques described by O. L. Brekke, *Deodorization, in Handbook of Soy Oil Processing and Utilization*, Erickson, D. R. et al. eds., pp. 155-191 published by the American Soybean Association and the American Oil Chemists' Society; or by Bailey's Industrial Oil and Fat Products, 5th ed., Vol. 2 (pp. 537-540) and Vol. 4 (pp. 339-390), Hui, Y. H. ed., published by John Wiley and Sons, Inc. Deodorization at ambient temperature can also be used as it will remove air from oil, which causes oxidation of oil. Other deodorization processes are described in U.S. Pat. Nos. 6,172,248 and 6,511,690.

The present application relates to the removal of constituents which cause or arise from fat or oil degradation from a fat or oil substrate prior to the substrate's contacting an esterification, transesterification or interesterification enzyme. Preferably, removal of constituents which cause or arise from fat or oil degradation is accomplished via deodorization. However, deodorization as used in the present invention is not limited to removal of the above described constituents which cause or arise from fat or oil degradation. Other characterized constituents which cause or arise from fat or oil degradation will be recognized by the skilled artisan and can also be removed by deodorization as used in the present invention. Other, as-of-yet uncharacterized constituents which cause or arise from fat or oil degradation can also be removed by deodorization as used in the present invention.

According to the method of the present invention, deodorization greatly improves the productivity of enzymatic transesterification or esterification by purifying the substrate fat or oil to extend the useful life of the enzyme. Constituents which cause or arise from fat or oil degradation can detrimentally affect lipase enzymatic activity. Hence, the invention relates to using deodorization to purify the substrate fat or oil prior to esterification, transesterification or interesterification enzymatic reaction for the purpose of prolonging the useful life of the enzyme. It is also beneficial to prevent the substrate oil from oxidation by keeping the oil under inert gases, such as nitrogen, carbon dioxide or helium. The esterified, transesterified or interesterified products of the present invention can also be deodorized after the treatment with enzyme.

The invention relates to a method of making an esterified, transesterified or interesterified product comprising:

(a) forming an initial substrate comprising one or more fats or oils;

(b) deodorizing the initial substrate thereby reducing the constituents which cause or arise from fat or oil degradation in the initial substrate and thereby producing a deodorized substrate;

(c) contacting the deodorized substrate with an enzyme thereby making the esterified, transesterified or interesterified product;

wherein the half-life of the enzyme is prolonged.

The deodorizing can be a batch deodorization process, a semi-continuous deodorization process, or a continuous deodorization process. The deodorizing can occur from 25° C. to 320° C.; from 100° C. to 300° C.; or from 150° C. to 270° C. The deodorizing can occur at a pressure of 0 to 760 torr, or at a pressure of 0 to 50, 0 to 40, 0 to 30, 0 to 20, 0 to 10, or 1 to 10 torr. The deodorization holding time can be from 5 minutes to 10 hours; or from 30 minutes to 3 hours. The deodorization stripping gas can be steam, and the stripping steam ratio can be 1-15 wt % of the initial substrate; or 1-5 wt % of the initial substrate. The method of making an esterified, transesterified or interesterified product can further comprise preventing oxidative degradation of the initial substrate, the deodorized substrate, the esterified, transesterified or interesterified product or the enzyme. The initial substrate can be partially or fully hydrogenated processed fats or oils, or fractionated fats or oils thereof. The initial substrate could have been previously deodorized.

Preferably, deodorization of the present invention reduces the peroxide value (PV) of the fat or oil sample to less than 1, 2, 3, 4, 5, 6, 7, 8, 9 or 10 mEq/kg oil. More preferably, deodorization reduces the PV value of the fat or oil sample to less than 1, 2, 3, 4 or 5 mEq/kg oil. Most preferably, deodorization reduces the PV value of the fat or oil sample to less than 1 or 2 mEq/kg oil, or to zero mEq/kg oil or an undetectable PV level.

The one or more unrefined and/or unbleached fats or oils can comprise butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, tallow or other animal fat, canola oil, castor oil, coconut oil, coriander oil, corn oil, cottonseed oil, hazlenut oil, hempseed oil, linseed oil, mango kernel oil, meadowfoam oil, neat's foot oil, olive oil, palm oil, palm kernel oil, palm olein, palm stearin, palm kernel olein, palm kernel stearin, peanut oil, rapeseed oil, rice bran oil, safflower oil, sasanqua oil, soybean oil, sunflower seed oil, tall oil, tsubaki oil, vegetable oils, marine oils which can be converted into plastic or solid fats such as menhaden, candlefish oil, cod-liver oil, orange roughy oil, pile herd, sardine oil, whale and herring oils, 1,3-dipalmitoyl-2-monooleine (POP), 1(3)-palmitoyl-3(1)-stearoyl-2-monooleine (POSt), 1,3-distearoyl-2-monooleine (StOSt), triglyceride, diglyceride, monoglyceride, behenic acid triglyceride, trioleine, tripalmitine, tristearine, triglycerides of medium chain fatty acids, or combinations thereof.

The enzyme can be a lipase obtained from a cultured eukaryotic or prokaryotic cell line, such as a 1,3-selective lipase or a non-selective lipase.

The method of making an esterified, transesterified or interesterified product can further comprise:

(d) monitoring enzymatic activity by measuring one or more physical properties of the esterified, transesterified or interesterified product;

(e) optionally adjusting the temperature or process flow rate of the initial substrate in response to changes in the physical properties thereby increasing the amount of esterified, transesterified or interesterified product; and (f) optionally adjusting the temperature or process flow rate of the deodorized substrate in response to changes in the physical properties thereby increasing the amount of esterified, transesterified or interesterified product.

The one or more physical properties includes the dropping point temperature of the product and the solid fat content temperature profile of the product.

The esterified, transesterified or interesterified product can comprise 1,3-diglycerides.

The deodorized substrate can be mixed with monohydroxyl alcohols or polyhydroxyl alcohols prior to contacting the deodorized substrate with the purification medium or the enzyme, and the esterified, transesterified or interesterified product can be formed from the esterification, transesterification or interesterification of the monohydroxyl alcohols or polyhydroxyl alcohols. The monohydroxyl alcohols or the polyhydroxyl alcohols can be primary, secondary or tertiary alcohols of annular, straight or branched chain compounds. The monohydroxyl alcohols can be selected from the group consisting of methyl alcohol, isopropyl alcohol, allyl alcohol, ethanol, propanol, n-butanol, iso-butanol, sec-butanol, tert-butanol, n-pentanol, iso-pentanol, n-hexanol, hexadecyl alcohol or octadecyl alcohol. The polyhydroxyl alcohols can be selected from the group consisting of glycerol, propylene glycol, ethylene glycol, 1,2-propanediol and 1,3-propanediol.

The esterified, transesterified or interesterified product can be 1,3-diglycerides, such as those disclosed in U.S. Pat. No. 6,004,611.

The invention also relates to using a purification medium to reduce within a fat or oil substrate the constituents which cause or arise from fat or oil degradation. Accordingly, the method of making an esterified, transesterified or interesterified product can further comprise contacting the initial substrate or the deodorized substrate (fats or oils alone, or mixed with additional components such as esters, free fatty acids or alcohols) with one or more types of purification media thereby producing a purification media-processed substrate. The purification media can contact the substrate in one or more columns or in one or more batch slurry type reactions. The purification medium preferably comes into contact with the substrate prior to the substrate's contacting the enzyme.

The purification medium can be selected from the group consisting of activated carbon, coal activated carbon, wood activated carbon, peat activated carbon, coconut shell activated carbon, natural minerals, processed minerals, montmorillonite, attapulgite, bentonite, palygorskite, Fuller's earth, diatomite, smectite, hormite, quartz sand, limestone, kaolin, ball clay, talc, pyrophyllite, perlite, silica, sodium silicate, silica hydrogel, silica gel, fumed silica, precipitated silica, dialytic silica, fibrous materials, cellulose, cellulose esters, cellulose ethers, microcrystalline cellulose; alumina, zeolite, starches, molecular sieves, previously used immobilized lipase, diatomaceous earth, ion exchange resin, size exclusion chromatography resin, chelating resins, chiral resins, rice hull ash, reverse phase silica, and bleaching clays. Most preferably, the combination of the purification medium is a combination of the silica and coconut shell activated carbon.

The purification medium can be silica having a surface area from 200 to 750 $m^2/g$, a mesh value from 3 to 425, an average particle size from 4-200μ, an average pore radius from 20 to 150 Å, and an average pore volume from 0.68 to 1.15 $cm^3/g$. The silica can be 35-60 mesh with an average pore size of about 60 Å.

The method of making an esterified, transesterified or interesterified product can further comprise:

(e) monitoring enzymatic activity by measuring one or more physical properties of the esterified, transesterified or interesterified product;

(f) optionally adjusting the temperature or process flow rate of the initial substrate in response to changes in the physical properties thereby increasing the amount of esterified, transesterified or interesterified product;

(g) optionally adjusting the temperature or process flow rate of the deodorized substrate in response to changes in the physical properties thereby increasing the amount of esterified, transesterified or interesterified product; and (h) optionally adjusting the temperature or process flow rate of the purification media-processed substrate in response to changes in the physical properties thereby increasing the amount of esterified, transesterified or interesterified product.

The one or more physical properties can include the dropping point temperature of the product, or the solid fat content temperature profile of the product.

The one or more types of purification media and the enzyme can be packed together or separately in one or more columns through which the initial substrate, the deodorized substrate or the esterified, transesterified or interesterified product flows. The columns can be jacketed columns in which the temperature of one or more of the initial substrate, the deodorized substrate, the purification media-processed substrate, the one or more types of purification media, the enzyme or the esterified, transesterified or interesterified product can be regulated. The purification media-processed substrate can be prepared by mixing the initial substrate or the deodorized substrate with the one or more types of purification media in a tank for a batch slurry purification reaction or mixing the initial substrate or the deodorized substrate in a series of tanks for a series of batch slurry purification reactions. The purification media-processed substrate can be separated from the one or more types of purification media via filtration, centrifugation or concentration prior to reacting the purification media-processed substrate with the enzyme.

The method of making an esterified, transesterified or interesterified product can further comprise mixing the deodorized substrate and/or the purification media-processed substrate with the enzyme in one or more tanks for a batch slurry reaction, or flowing the deodorized substrate and/or the purification media-processed substrate through a column containing the enzyme. A bed of the one or more types of purification media can be placed upon a bed of the enzyme within a column.

The initial substrate, the deodorized substrate, the purification media-processed substrate, the esterified, transesterified or interesterified product and the enzyme can be in an inert gas environment. The inert gas can be selected from the group consisting of $N_2$, $CO_2$, He, Ar, and Ne. Preferably, the methods of the present invention further comprises preventing oxidative degradation of the initial substrate, the deodorized substrate, the purification media-processed substrate, the esterified, transesterified or interesterified product or the enzyme. The method of making an esterified, transesterified or interesterified product can further comprise preventing oxidative degradation to the initial substrate, the deodorized substrate, the purification media-processed substrate, the esterified, transesterified or interesterified product or the enzyme.

The skilled artisan would recognize that in respect to the method of making an esterified, transesterified or interesterified product, any combination of the above described particulars pertaining to deodorization options (e.g., flow rate, residence or holding time, temperature, pressure, choice of inert gas), initial substrate, components (e.g., free fatty acids, nonglyceride esters, alcohols) optionally added to the deodorized substrate or the purification media-processed substrate, enzyme, monitoring or adjusting methods, fats or oils produced, use of columns or batch slurry reactions, and purification medium are useful in the present invention. The substrate can be deodorized and then come into contact with purification medium, or vice versa.

The initial substrate can be composed of one or more types of fat or oil and have its physical properties modified in an esterification, transesterification or interesterification process known as randomization. Nonselective enzymes randomize at all three positions on a glyceride; but 1,3-specific lipases randomize only at the 1 and 3 positions on a glyceride. For example, when fully hydrogenated palm kernel oil is treated with lipase capable of randomization, the components of the product have different physical properties. Both 1,3-specific lipases and nonselective lipases such as *Candida cylindracae* lipase are capable of this randomizing process.

Transesterification or esterification is affected by an enzyme, which is preferably obtained from a cultured eukaryotic or prokaryotic cell line. The enzyme can be a lipase that is specific or unspecific with respect to its substrate. Preferably, the lipase is a 1,3-selective lipase, which catalyzes esterification or transesterification of the terminal esters in the 1 and 3 positions of a glyceride. The lipase can also preferably be a non-selective, nonspecific lipase.

There are many microorganisms from which lipases useful in the present invention are obtained. U.S. Pat. No. 5,219,733 lists examples of such microorganisms including those of the genus *Achromobacter* such as *A. iofurgus* and *A. lipolyticum*, the genus *Chromobacterium* such as *C. viscosum* var. *paralipolyticum*; the genus *Corynebacterium* such as *C. acnes*; the genus *Staphylococcus* such as *S. aureus*; the genus *Aspergillus* such as *A. niger* and *A. oryzae*; the genus *Candida* such as *C. cylindracea, C. antarctica b, C. rosa* and *C. rugosa*; the genus *Humicora* such as *H. lanuginosa*; the genus *Penicillium* such as *P. caseicolum, P. crustosum, P. cyclopium* and *P. roqueforti*; the genus *Torulopsis* such as *T. ernobii*; the genus *Mucor* such as *M. miehei, M. japonicus* and *M. javanicus*; the genus *Bacillus* such as *B. subtilis*; the genus *Thermomyces* such as *T. ibadanensis* and *T. lanuginosa* (see Zhang, H. et al. J.A.O.C.S. 78: 57-64 (2001)); the genus *Rhizopus* such as *R. delemar, R. japonicus, R. arrhizus* and *R. neveus*; the genus *Pseudomonas* such as *P. aeruginosa, P. fragi, P. cepacia, P. mephitica* var. *lipolytica* and *P. fluorescens*; the genus *Alcaligenes*; the genus *Rhizomucor* such as *R. miehei*; the genus *Humicolo* such as *H. rosa*; and the genus *Geotrichum* such as *G. candidum*. Several lipases obtained from these organisms are commercially available as purified enzymes. The skilled artisan would recognize other enzymes capable of affecting esterification, transesterification or interesterification including other lipases useful for the present invention.

Lipases obtained from the organisms above are immobilized for the present invention on suitable carriers by a usual method known to persons of ordinary skill in the art. U.S. Pat. Nos. 4,798,793; 5,166,064; 5,219,733; 5,292,649; and 5,773,266 describe examples of immobilized lipase and methods of preparation. Examples of methods of preparation include the entrapping method, inorganic carrier covalent bond method, organic carrier covalent bond method, and the adsorption method. The lipase used in the examples below were obtained from Novozymes (Denmark) but can be substituted with purified and/or immobilized lipase prepared by others. The present invention also contemplates using crude enzyme preparations or cells of microorganisms capable of over expressing lipase, a culture of such cells, a substrate enzyme solution obtained by treating the culture, or a composition containing the enzyme.

U.S. Pat. Nos. 4,940,845 and 5,219,733 describe the characteristics of several useful carriers. Useful carriers are preferably microporous and have a hydrophobic porous surface. Usually, the pores have an average radius of about 10 Å to about 1,000 Å, and a porosity from about 20 to about 80% by volume, more preferably, from about 40 to about 60% by volume. The pores give the carrier an increased enzyme bonding area per particle of the carrier. Examples of preferred inorganic carriers include porous glass, porous ceramics, celite, porous metallic particles such as titanium oxide, stainless steel or alumina, porous silica gel, molecular sieve, active carbon, clay, kaolinite, perlite, glass fibers, diatomaceous earth, bentonite, hydroxyapatite, calcium phosphate gel, and alkylamine derivatives of inorganic carriers. Examples of preferred organic carriers include microporous Teflon, aliphatic olefinic polymer (e.g., polyethylene, polypropylene, a homo- or copolymer of styrene or a blend thereof or a pretreated inorganic support) nylon, polyamides, polycarbonates, nitrocellulose and acetylcellulose. Other suitable organic carriers include hydrophillic polysaccharides such as agarose gel with an alkyl, phenyl, trityl or other similar hydrophobic group to provide a hydrophobic porous surface (e.g., "Octyl-Sepharose CL-4B", "Phenyl-Sepharose CL-4B", both products of Pharmacia Fine Chemicals (Kalamazoo, Mich.). Microporous adsorbing resins include those made of styrene or alkylamine polymer, chelate resin, ion exchange resin such a "DOWEX MWA-1" (weakly basic anion exchange resin manufactured by the Dow Chemical Co., having a tertiary amine as the exchange group, composed basically of polystyrene chains cross linked with divinylbenzene, 150 Å in average pore radius and 20-50 mesh in particle size), and hydrophilic cellulose resin such as one prepared by masking the hydrophilic group of a cellulosic carrier, e.g., "Cellulofine GC700-m" (product of Chisso Corporation (Tokyo, Japan), 45-105 μm in particle size).

The esterification, transesterification or interesterification can be conducted in a column or in batch slurry type reactions as described in the Examples section below. In the batch slurry reactions, the enzyme and substrates are mixed vigorously to ensure a good contact between them. Preferably, the transesterification or esterification reaction is carried out in a fixed bed reactor with immobilized lipases.

The fatty acid groups described herein can be added to the deodorized substrate or the purification media-processed substrate to esterify alcoholic groups present on glycerides of the initial substrate, or alcoholic groups of other compounds (e.g., alcohols or esters) added to the deodorized substrate or the purification media-processed substrate. Glycerides having any of the fatty acid groups as described herein can also be used in the initial substrate; and other esters having any of the fatty acid groups described herein can be added to the deodorized or purification media-processed substrate. Such fatty acids include saturated straight-chain or branched fatty acid groups, unsaturated straight-chain or branched fatty acid groups, hydroxy fatty acid groups, and polycarboxylic acid groups, or contain non-carbon substituents including oxygen, sulfur or nitrogen. The fatty acid groups can be naturally occurring, processed or refined from natural products or synthetically produced. Although there is no upper or lower limit for the length of the longest carbon chain in useful fatty acids, it is preferable that their length is about 6 to about 34 carbons long. Specific fatty acid groups useful for the present invention can be formed from the fatty acids described in U.S. Pat. Nos. 4,883,684; 5,124,166; 5,149,642; 5,219,733; 5,399,728.

Examples of useful saturated straight-chain fatty acid groups having an even number of carbon atoms can be formed from the fatty acids described in U.S. Pat. No. 5,219,733 including acetic acid, butyric acid, caproic acid, caprylic acid, capric acid, lauric acid, myristic acid, palmitic acid, stearic acid, arachic acid, behenic acid, lignoceric acid, hexacosanoic acid, octacosanoic acid, triacontanoic acid and n-dotriacontanoic acid, and those having an odd number of carbon atoms, such as propionic acid, n-valeric acid, enanthic acid, pelargonic acid, hendecanoic acid, tridecanoic acid, pentadecanoic acid, heptadecanoic acid, nonadecanoic acid, heneicosanoic acid, tricosanoic acid, pentacosanoic acid and heptacosanoic acid.

Examples of useful saturated branched fatty acid groups can be formed from fatty acids described in U.S. Pat. No. 5,219,733 including isobutyric acid, isocaproic acid, isocaprylic acid, isocapric acid, isolauric acid, 11-methyldodecanoic acid, isomyristic acid, 13-methyl-tetradecanoic acid, isopalmitic acid, 15-methyl-hexadecanoic acid, isostearic acid, 17-methyloctadecanoic acid, isoarachic acid, 19-methyl-eicosanoic acid, a-ethyl-hexanoic acid, a-hexyldecanoic acid, a-heptylundecanoic acid, 2-decyltetradecanoic acid, 2-undecyltetradecanoic acid, 2-decylpentadecanoic acid, 2-undecylpentadecanoic acid, and Fine oxocol 1800 acid (product of Nissan Chemical Industries, Ltd.)

Examples of useful saturated odd-carbon branched fatty acid groups can be formed from fatty acids described in U.S. Pat. No. 5,219,733 including anteiso fatty acids terminating with an isobutyl group, such as 6-methyl-octanoic acid, 8-methyl-decanoic acid, 10-methyl-dodecanoic acid, 12-methyl-tetradecanoic acid, 14-methyl-hexadecanoic acid, 16-methyl-octadecanoic acid, 18-methyl-eicosanoic acid, 20-methyl-docosanoic acid, 22-methyl-tetracosanoic acid, 24-methyl-hexacosanoic acid and 26-methyloctacosanoic acid.

Examples of useful unsaturated fatty acid groups can be formed from fatty acids described in U.S. Pat. No. 5,219,733 including 4-decenoic acid, caproleic acid, 4-dodecenoic acid, 5-dodecenoic acid, lauroleic acid, 4-tetradecenoic acid, 5-tetradecenoic acid, 9-tetradecenoic acid, palmitoleic acid, 6-octadecenoic acid, oleic acid, 9-octadecenoic acid, 11-octadecenoic acid, 9-eicosenoic acid, cis-11-eicosenoic acid, cetoleic acid, 13-docosenoic acid, 15-tetracosenoic acid, 17-hexacosenoic acid, 6,9,12,15-hexadecatetraenoic acid, linoleic acid, linolenic acid, α-eleostearic acid, β-eleostearic acid, punicic acid, 6,9,12,15-octadecatetraenoic acid, parinaric acid, 5,8,11,14-eicosatetraenoic acid, 5,8,11,14,17-eicosapentaenoic acid (EPA), 7,10,13,16,19-docosapentaenoic acid, 4,7,10,13,16,19-docosahexaenoic acid (DHA) and the like.

Examples of useful hydroxy fatty acid groups can be formed from fatty acids described in U.S. Pat. No. 5,219,733 including α-hydroxylauric acid, α-hydroxymyristic acid, α-hydroxypalmitic acid, α-hydroxystearic acid, ω-hydroxylauric acid, α-hydroxyarachic acid, 9-hydroxy-12-octadecenoic acid, ricinoleic acid, α-hydroxybehenic acid, 9-hydroxy-trans-10,12-octadecadienic acid, kamolenic acid, ipurolic acid, 9,10-dihydroxystearic acid, 12-hydroxystearic acid and the like.

Examples of useful polycarboxylic acid fatty acid groups can be formed from fatty acids described in U.S. Pat. No. 5,219,733 including oxalic acid, citric acid, malonic acid, succinic acid, glutaric acid, adipic acid, pimelic acid, suberic acid, azelaic acid, sebacic acid, D,L-malic acid and the like.

Preferably, the fatty acid groups have carbon chains from 4 to 34 carbons long. More preferably, the fatty acid groups have carbon chains from 4 to 26 carbons long. Most preferably, the fatty acid groups have carbon chains from 4 to 22 carbons long. Preferably the fatty acid groups are formed from the following group of free fatty acids: palmitic acid, stearic acid, oleic acid, linoleic acid, linolenic acid, arachidonic acid, erucic acid, caproic acid, caprylic acid, capric acid, eicosapentanoic acid (EPA), docosahexaenoic acid (DHA), lauric acid, myristic acid, 5-eicosenoic acid, butyric acid, g-linolenic acid and conjugated linoleic acid. Fatty acid groups formed from fatty acids derived from various plant and animal fats and oils (such as fish oil fatty acids) and processed or refined fatty acids from plant and animal fats and oils (such as fractionated fish oil fatty acids in which EPA and DHA are concentrated) can also be added. Fatty acid groups can also be formed from medium chain fatty acids (as described by Merolli, A. et al., INFORM, 8:597-603 (1997)). Also preferably, the fatty acid groups are formed from free fatty acids having carbon chains from 4 to 36, 4 to 24 or 4 to 22 carbons long.

Alcohols or esters of alcohols can also be added to the deodorized substrate or the purification media-processed substrate. These alcohols and esters can be esterified, transesterified or interesterified by acid groups present on glycerides of the initial substrate. Alternatively, these alcohols or esters thereof can be esterified, transesterified or interesterified by free fatty acids or esters added to the deodorized substrate or purification media-processed substrate. "Esters" include any of the alcohols described herein esterified by any of the fatty acids described herein.

Examples of alcohols useful in the present invention include monohydroxyl alcohols or polyhydroxyl alcohols. The monohydroxyl alcohols can be primary, secondary or tertiary alcohols of annular, straight or branched chain compounds with one or more carbons such as methyl alcohol, isopropyl alcohol, allyl alcohol, ethanol, propanol, n-butanol, iso-butanol, sec-butanol, tert-butanol, n-pentanol, iso-pentanol, n-hexanol, hexadecyl alcohol or octadecyl alcohol. The hydroxyl group can be attached to an aromatic ring, such as phenol. Examples of polyhydroxyl alcohols includes glycerol, propylene glycol, ethylene glycol, 1,2-propanediol and 1,3-propanediol.

U.S. Pat. No. 5,219,733 indicates other alcohols useful for the present invention. These alcohols include, but are not limited to 14-methylhexadecanol-1, 16-methyloctadecanol-1, 18-methylnonadecanol, 18-methyleicosanol, 20-methylheneicosanol, 20-methyldocosanol, 22-methyltricosanol, 22-methyltetracosanol, 24-methylpentacosanol-1 and 24-methylhexacosanol.

Examples of useful esters other than glycerides include wax esters, alkyl esters such as methyl, ethyl, isopropyl, hexadecyl or octadecyl esters, aryl esters, propylene glycol esters, ethylene glycol esters, 1,2-propanediol esters and 1,3-propanediol esters. Esters can be formed from the esterification, transesterification or interesterification of monohydroxyl alcohols or polyhydroxyl alcohols by the free fatty acids, fats or oils as described herein.

Processed fats and oils such as hydrogenated or fractionated fats and oils can also be used. Examples of fractionated fats include palm olein, palm stearin, palm kernel olein, and palm kernel stearin. Fully or partially hydrogenated, saturated, unsaturated or polyunsaturated forms of the above listed fats, oils, triglycerides or diglycerides are also useful for the present invention. For the method of this invention, the described fats, oils, triglycerides or diglycerides are usable singly, or at least two of them can be used in admixture.

In addition to deodorization, purification using a purification medium can be performed to prolong the half-life of the enzyme. Use of the purification media can occur before or after deodorization. One example of the purification means is silica gel packed in a column for pre-column purification of the substrate. However, it is also contemplated that the silica gel can be provided as a packed bed on top of the column packed lipase. The purification medium of the present invention is preferably silica having a surface area from 200 to 750 $m^2/g$, a mesh value from 3 to 425, an average particle size from 4-200μ, an average pore radius from 20 to 150 Å, and an average pore volume from 0.68 to 1.15 $cm^3/g$. Also preferably the silica gel is 35-60 mesh with an average pore size of 60 Å. Most preferably, the purification media is a combination of silica and coconut shell activated carbon.

It is also contemplated that the purification medium useful in the present invention can be selected from one of the following: activated carbon, coal activated carbon, wood activated carbon, peat activated carbon, coconut shell activated carbon, natural minerals, processed minerals, montmorillonite, attapulgite, bentonite, palygorskite, Fuller's earth, diatomaceous earth, diatomite, smectite, hormite, quartz sand, limestone, kaolin, clays, ball clay, talc, pyrophyllite, perlite, silica, sodium silicate, silica hydrogel, silica gel, fumed silica, precipitated silica, dialytic silica, TriSyl® silica (Grace Davison, Columbia, Md.), fibrous materials, cellulose, cellulose esters, cellulose ethers, microcrystalline cellulose, Avicel® (FMC BioPolymer), alumina, zeolite, starches, molecular sieves, previously used immobilized lipase, ion exchange resin, size exclusion chromatography resin, chelating resins, chiral resins, rice hull ash, reverse phase silica, and bleaching clays. The purification medium can be resinous, granulated, particulate, membranous or fibrous.

In the method of the present invention, one or more types of purification media and the lipase are packed into one or more columns. If multiple types of purification media are used, they can be mixed together and packed into a single column or kept separate in different columns. In an alternative embodiment, one or more types of purification media are placed upon a bed of packed lipase within a column. Alternatively, the lipase can be kept separate from the purification media by packing it in its own column. More than one type of purification media can be used for purposes of removing different kinds of impurities in the initial substrate. The columns and other fluid conduits can be jacketed so as to regulate the temperature of the initial substrate, the deodorized substrate, the purification media-processed substrate, the purification media or the enzyme. The purification media can be regenerated for repeated use.

Also in the method of the present invention, the purification media-processed substrate is prepared by mixing the initial substrate or the deodorized substrate with one or more types of purification media in a tank for a batch slurry type purification reaction or mixing the initial substrate in a series of tanks for a series of batch slurry type purification reactions. In these batch slurry type purification reactions, the different types of purification media can be kept separate or can be combined. After reacting with one type of purification medium (or specific mixture of purification media), the initial substrate is separated from the purification medium (or media) via filtration, centrifugation or concentration. After this separation step, the initial substrate is further purified with other purification media or serves as purification media-processed substrate and is reacted with lipase. The purification media-processed substrate prepared by this batch slurry type purification reaction method can be reacted with lipase in a tank for batch slurry type transesterification or esterification. Alternatively, the purification media-processed substrate can be caused to flow through a lipase column. The reacting tanks, columns and other fluid conduits can be jacketed so as to regulate the temperature of the initial substrate, the deodorized substrate, the purification media-processed substrate, the purification media or the enzyme. Other manners of temperature regulation, such as heating/cooling coils or temperature controlled rooms, are contemplated and well known in the art. The purification media can be regenerated for repeated use.

Lipase enzymatic activity is also affected by factors such as temperature, light and moisture content. Temperature is controlled as described above. Light can be kept out by using various light blocking or filtering means known in the art. Moisture content, which includes ambient atmospheric moisture, is controlled by operating the process as a closed system. Where the deodorization process uses steam as the stripping agent, the deodorization process can be kept isolated from the enzyme. Because deodorization is performed at high temperature and under vacuum, moisture content in the deodorized oil is very low. Where the deodorization process uses an inert gas as the stripping agent, the deodorization process is optionally kept isolated from the enzyme. Alternatively, a bed of nitrogen gas (or other inert gas) can be placed on top of the bed or column containing either purification medium or enzyme. These techniques have the added benefit of keeping atmospheric oxidative species (including oxygen) away from the substrate, product or enzyme.

Immobilized lipase can be mixed with initial, deodorized or purification media-processed substrate to form a slurry which is packed into a suitable column. Alternatively, substrate can flow through a pre-packed enzyme column. The temperature of the substrate is regulated so that it can continuously flow though the column for contact with the transesterification or esterification enzyme. If solid or very viscous fats, oils, triglycerides or diglycerides are used, the substrate is heated to a fluid or less viscous state. The substrate can be caused to flow through the column(s) under the force of gravity, by using a peristaltic or piston pump, under the influence of a suction or vacuum pump, or using a centrifugal pump. The transesterified fats and oils produced are collected and the desired glycerides are separated from the mixture of reaction products by methods well known in the art. This continuous method involves a reduced likelihood of permitting exposure of the substrates to air during reaction and therefore has the advantage that the substrates will not be exposed to moisture or oxidative species. Alternatively, reaction tanks for batch slurry type production as described above can also be used. Preferably, these reaction tanks are also sealed from air so as to prevent exposure to oxygen, moisture, or other ambient oxidizing species.

The method of the present invention also relates to monitoring enzymatic activity by measuring one or more physical properties of the esterified, transesterified or interesterified product; optionally adjusting the temperature or process flow rate of the initial substrate in response to changes in the physical properties thereby increasing the proportion of esterified, transesterified or interesterified product relative to the initial substrate; optionally adjusting the temperature or process flow rate of the deodorized substrate in response to changes in the physical properties thereby increasing the proportion of esterified, transesterified or interesterified product relative to the deodorized substrate; optionally adjusting the temperature or process flow rate of the purification media-processed substrate in response to changes in the physical properties thereby increasing the proportion of esterified, transesterified or interesterified product relative to the purification media-processed substrate; and optionally adjusting the amount and type of the one or more types of purification media in response to changes in the physical properties to increase the proportion of esterified, transesterified or interesterified product relative to the substrate.

In the present invention, changes in enzymatic activity are monitored by following changes in the physical properties of the product. As the enzymatic activity decreases, less of the substrate is converted into product via esterification, transesterification or interesterification. Consequently, as the enzymatic activity decays, the physical properties of the product increasingly resemble the physical properties of the components of the substrate. The skilled artisan recognizes that by following changes in physical properties, the parameters of the esterified, transesterified or interesterified production process can be adjusted, thereby increasing the proportion of esterified, transesterified or interesterified product relative to the substrate.

The Mettler dropping point (MDP) is one example of a physical property which can be measured to follow changes in enzymatic activity. The MDP is determined using Mettler Toledo, Inc. (Columbus, Ohio) thermal analysis instruments according to the American Oil Chemists Society Official Method #Cc 18-80. The MDP is the temperature at which a mixture of fats or oils becomes fluid. The product's solid fat content (SFC) temperature profile is another useful physical property for tracking changes in enzymatic activity. SFC can be measured according to American Oil Chemists Society Official Method #Cd 16b-93. Following changes in optical spectra is another way to monitor changes in enzymatic activity. The substrate and product each have a characteristic optical spectrum. As the lipase activity decays, the amount of product that gives rise to spectroscopic signals attributable to esterified, transesterified or interesterified product (and not attributable to substrate) diminishes. All of these properties are measured using techniques well known in the art, and are useful in following changes in enzymatic activity.

For example, as the lipase enzymatic activity decays, less substrate is converted into product resulting in an increased substrate:product ratio. This increased ratio is manifested in a change of physical properties of the outflowing product tending towards the physical properties of the non-esterified or non-transesterified substrate. To minimize this change, the flow rate of the substrate is reduced so that it is exposed for a longer period of time to the packed lipase. The flow rate reduction increases the product:substrate ratio and consequently the physical properties of the outflowing fats or oils reflect that of esterified, transesterified or interesterified product. Other process parameters that can be altered include the flow rate, temperature or pressure of the initial substrate, deodorized substrate, or the purification media-processed substrate.

Where purification media-processed substrate is reacted with lipase in a tank for batch slurry type production, changes in the product's physical properties can also be monitored as described above. In a batch slurry type process, an optimized duration of time is determined for contacting the initial substrate or deodorized substrate with the purification medium (or media). An optimized time is also determined for contacting the deodorized substrate or purification media-processed substrate with enzyme.

Thus, the present invention involves monitoring enzymatic activity by measuring one or more physical properties of the product after having flowed through the lipase, adjusting flow rate, column residence time, or temperature of the initial substrate, deodorized substrate, or purification media-processed substrate, and adjusting the deodorization parameters or the amount and type of the purification medium in response to changes in the physical properties to increase the proportion of esterified, transesterified or interesterified fats or oils in the product.

The esterified, transesterified or interesterified product can be subjected to usual oil refining processes including fractionation, separation or purification process, or additional deodorization processing. The method of the present invention can produce 1,3-diglycerides. Also preferably, the process produces esterified, transesterified or interesterified fats with no or reduced trans fatty acids for margarine, shortening, and other confectionery fats such as cocoa butter substitute. The product of the present process can be separated from any free fatty acid or other by-products by refining techniques well known in the art. In the case of batch slurry type methods, the desired product can be separated using a suitable solvent such as ether, removing the fatty acid material with an alkali, dehydrating and drying the solvent layer, and removing the solvent from the layer. The desired product can be purified, for example, by column chromatography. The desired products thus obtained are usable for a wide variety of culinary applications.

The following examples show the effect of the substrate pretreatment on the enzyme productivity.

EXAMPLES

The examples described below show that productivity of the enzymatic transesterification or esterification is improved greatly by deodorization and/or purification of the substrate oil. The following examples are illustrative only and are not intended to limit the scope of the invention as defined by the appended claims.

In Example 1 and 2, the transesterification was performed without any pretreatment. In both of the examples, a rapid loss of enzyme activity was observed at the beginning of the column operation. Estimated half-lives during this period of rapid activity loss were 6 to 14 days; then, the rate of activity loss slowed, giving half-lives estimations of 28 to 30 days. A rapid loss of activity was observed, again, after running the column for about 30 days. In contrast, Example 3 demonstrates that the operation with a silica purification column did not have an initial period of rapid enzyme activity loss. Rather, the half-life estimation was about 30 days; then, the activity loss even slowed to give about 50-day estimation for the second half-life.

Example 1

22 g of enzyme (Novozymes' Lipozyme® TL IM) was mixed with liquid soybean oil and packed into a jacketed glass column (2.7-cm diameter). The soy oil was flushed out by pumping the actual substrate (fully hydrogenated soy oil: liquid soy oil=27:73). The column and the substrate were maintained at 65° C. Extent of enzyme reaction could be monitored very well by the change of melting properties of the substrate and products, which was measured as Mettler dropping point (MDP). Oil flow of the column was adjusted so as to have the products' MDP at 117-118° F. Enzyme activity was calculated by comparing the flow rates at which the products have similar MDPs near 117-118° F.

Figure 1:
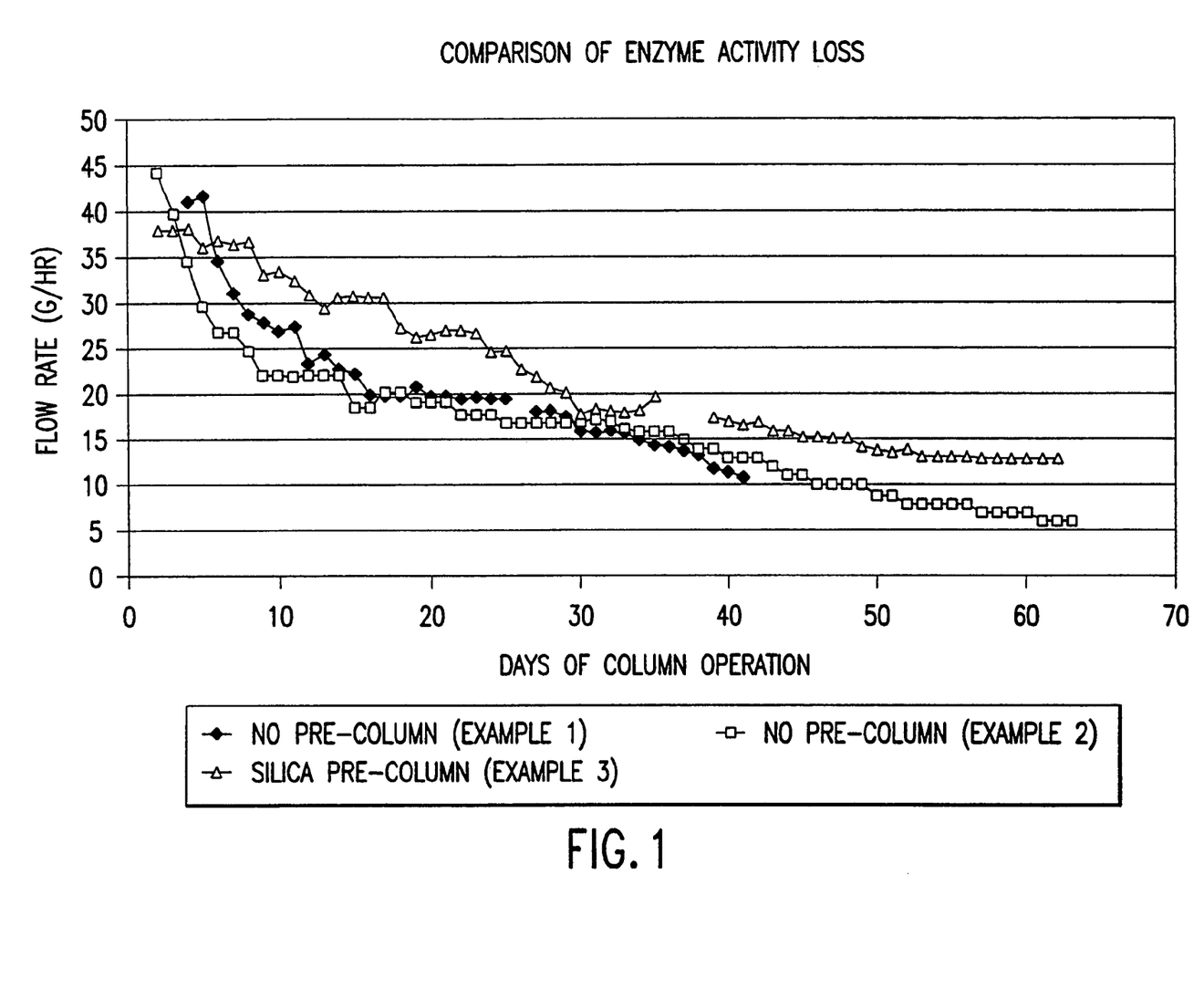
FIG. 1 is a graph showing the decay of lipase enzymatic activity as measured by the decrease in product flow rate where a piston pump is used without purification medium (closed diamonds), where a peristaltic pump is used without purification medium (open squares), and where a piston pump is used with purification medium (open triangles).

Table 1 summarizes the results. There was a quick activity drop for the first 2 weeks; then the activity drop slowed down. The enzyme activity at Day 13 was about 60% level of that at Day 4. There was another quick activity drop after Day 30. FIG. 1 (closed diamonds) shows the data in greater detail.

TABLE 1

Summary Results of the Column Operation Without Silica Pretreatment as in Example 1

| | |
|---|---|
| ~Day 4: | Flushing out soy oil from the column & flow rate adjustment |
| Day 4~Day 7: | 25% activity drop in 3 days (6-day half-life estimation) |
| Day 7~Day 10: | 13% drop in 3 days (12-day half-life estimation) |
| Day 10~Day 13: | 11% drop in 3 days (14-day half-life estimation) |
| Day 13~Day 25: | 20% drop in 12 days (30-day half-life estimation) |
| Day 26 | Total draining of column happened. |
| Day 13~Day 35: | 40% drop in 22 days (29-day half-life estimation) |
| Day 27~Day 35: | 20% drop in 8 days (20-day half-life estimation) |
| Day 36~Day 41: | 25% drop in 5 days (10-day half-life estimation) |

Example 2

An enzyme column was prepared and run in the same way as described in Example 1, except using a peristaltic pump instead of a piston pump, for replication. Table 2 summarizes the results. As in Example 1, there was a quick activity drop for the first 2 weeks; then, the activity drop slowed down.

However, there was another quick activity drop after Day 35. FIG. 1 (open squares) shows the data in greater detail.

TABLE 2

Summary Results of the Column Operation Without Silica Pretreatment as in Example 2

| ~Day 2: | Flushing out soy oil & flow rate adjustment |
|---|---|
| Day 2~Day 8: | 44% activity drop in 6 days (7-day half-life estimation) |
| Day 2~Day 12: | 49% drop in 10 days (10-day half-life estimation) |
| Day 12~Day 35: | 28% drop in 23 days (40-day half-life estimation) |
| Day 35~Day 46: | 37% drop in 11 days (15-day half-life estimation) |
| Day 45~Day 51: | 18% drop in 6 days (16-day half-life estimation) |

Example 3

An enzyme column was prepared as described in Example 1 and 2, and 38 g of silica gel (35-60 mesh, 60 Å) was placed on top of the enzyme bed. Conditions for column operation and analysis were the same as in the previous examples. Table 3 summarizes the results.

There was no quick activity drop in the beginning of the column operation, and the half-life estimation at the time was about 30 days. Even longer half-life estimation was observed as the column was operating for an extended period. FIG. 1 (open triangles) shows the data in greater detail.

TABLE 3

Summary Results of the Column Operation with Silica Pre-Column Treatment

| ~Day 2: | Flushing out soy oil & flow rate adjustment |
|---|---|
| Day 2~Day 9: | 13% activity drop in 7 days (28-day half-life estimation) |
| Day 9~Day 34: | 46% drop in 25 days (27-day half-life estimation) |
| Day 34~Day 46: | 15% drop in 12 days (41-day half-life estimation) |
| Day 45~Day 60: | 15% drop in 15 days (50-day half-life estimation) |

Example 4

400 g of the substrate oil (fully hydrogenated soy oil:corn oil=27:73) in a 1-L flask was heated to 70° C. before adding 40 g of Novozymes' Lipozyme® TL IM lipase. The enzyme/oil slurry was stirred vigorously at the temperature, and samples were taken after 1, 2, 3, 4, 8 and 18 hours of reaction. After the batch reaction, the enzyme was separated from the product oil by filtering the slurry through a filter paper with 2.7-micron particle retention. Table 4 shows the SFC temperature profiles and free fatty acid contents of the samples. The batch reaction yielded more than 10 times greater free fatty acids. The reaction seemed to reach equilibrium after 8 hours of reaction.

TABLE 4

SFC Temperature Profiles and Free Fatty Acid (FFA) Contents of the Batch Reaction Samples

| SFC | 1 hr | 2 hr | 3 hr | 4 hr | 8 hr | 18 hr | Feed |
|---|---|---|---|---|---|---|---|
| 50° F. | 18.090 | 15.493 | 15.128 | 14.237 | 14.730 | 14.873 | 30.833 |
| 70° F. | 18.297 | 12.905 | 10.739 | 9.130 | 8.387 | 7.816 | 28.032 |
| 80° F. | 17.013 | 12.047 | 9.089 | 7.844 | 6.848 | 6.991 | 26.096 |
| 92° F. | 12.963 | 8.558 | 7.062 | 5.643 | 5.194 | 4.425 | 24.246 |
| 100° F. | 10.318 | 6.711 | 4.307 | 3.433 | 2.831 | 2.562 | 22.215 |
| % FFA | 4.88% | 5.02% | 5.36% | 5.27% | 5.49% | 5.47% | 0.066% |

Example 5

To determine the effect of deodorization on enzyme half-life, non-deodorized hydrogenated palm kernel oil was obtained and batch-deodorized at the lab and used for the enzyme column operation. Deodorization conditions were 30 min at 230° C. under 1-2 torr vacuum with about 5% steam/oil ratio. Peroxide values (PV) of the oils before and after deodorization were 0.5 and 0 meq/Kg oil, respectively. The oil was re-deodorized daily for the column operation. The half-life of the enzyme exposed to the lab-deodorized oil was 30 days; on the other hand, the half-life for the enzyme exposed to the non-deodorized oil was 7 days. Distillates from the deodorization, which contains impurities removed from oil, were recovered and added back to the non-deodorized oil for enzyme column operation. The oil with added-distillate inactivated the enzyme quickly (half-life was only 3 days). This example shows that the enzyme half-life can be affected greatly by the impurities in oil even with low PV.

Example 6

In another example, a substrate of a refined, bleached and deodorized (RBD) oil mixture was batch re-deodorized at the lab and used for the enzyme column operation. The substrate oil mixture consisted of 27% RBD fully hydrogenated soy oil (FHSBO) and 73% RBD soy oil. Deodorization conditions were 30 min at 240° C. under 1-2 torr vacuum with about 5% steam/oil ratio. Prior to re-deodorization, PVs of RBD FHSBO and RBD soy oil were 0.8 and 2.4 meq/Kg oil, respectively. However, the re-deodorized oil did not contain any peroxide. The oil was re-deodorized daily for the column operation. Half-life with the re-deodorized oil was 20 days; on the other hand, the one with non-redeodorized RBD substrate was only 9 days.

All publications mentioned above are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

I claim:

1. A method of making an esterified, transesterified or interesterified product comprising:
   (a) deodorizing an initial substrate, wherein said initial substrate comprises one or more fats or oils and contains constituents that cause or arise from fat or oil degradation, thereby reducing the constituents which cause or arise from fat or oil degradation in said initial substrate and thereby producing a deodorized substrate;

(b) contacting said deodorized substrate with a fat or oil modifying enzyme thereby making said esterified, transesterified or interesterified product;
wherein the half-life of said enzyme is prolonged.

2. The method of claim 1, wherein said initial substrate was previously deodorized.

3. The method of claim 1, wherein said deodorizing is a batch deodorization process, a semi-continuous deodorization process, or a continuous deodorization process.

4. The method of claim 1, wherein said deodorizing occurs from 25° C. to 320° C.

5. The method of claim 4, wherein said deodorizing occurs from 100° C. to 300° C.

6. The method of claim 5, wherein said deodorizing occurs from 150° C. to 270° C.

7. The method of claim 1, wherein said deodorizing occurs at a pressure of 0 to 760 torr.

8. The method of claim 7, wherein said deodorization occurs at a pressure of 1 to 10 torr.

9. The method of claim 1, wherein said initial substrate comprises butterfat, cocoa butter, cocoa butter substitutes, illipe fat, kokum butter, milk fat, mowrah fat, phulwara butter, sal fat, shea fat, borneo tallow, lard, lanolin, beef tallow, mutton tallow, animal fat, canola oil, castor oil, coconut oil, coriander oil, corn oil, cottonseed oil, hazlenut oil, hempseed oil, linseed oil, mango kernel oil, meadowfoam oil, neat's foot oil, olive oil, palm oil, palm kernel oil, palm olein, palm stearin, palm kernel olein, palm kernel steam, peanut oil, rapeseed oil, rice bran oil, safflower oil, sasanqua oil, soybean oil, sunflower seed oil, tall oil, tsubaki oil, marine oils which can be converted into plastic or solid fats, menhaden oil, candlefish oil, cod-liver oil, orange roughy oil, pile herd oil sardine oil, whale oil herring oil, 1,3-dipalmitoyl-2-monooleine (POP), 1(3)-palmitoyl-3(1)-stearoyl-2-monooleine (POSt), 1,3-distearoyl-2-monooleine (StOSt), triglyceride, diglyceride, monoglyceride, behenic acid triglyceride, trioleine, tripalmitine, tristearine, or combinations of any thereof.

10. The method of claim 1, wherein said enzyme is a lipase obtained from a cultured eukaryotic or prokaryotic cell line.

11. The method of claim 10, wherein said lipase is a 1,3-selective lipase.

12. The method of claim 1, wherein said esterified, transesterified or interesterified product comprises 1,3-diglycerides.

13. The method of claim 1, further comprising contacting said enzyme with said deodorized substrate in one or more jacketed columns; and, regulating the temperature of one or more of said initial substrate, said deodorized substrate, said esterified, transesterified or interesterified product, or said enzyme.

14. The method of claim 1, further comprising mixing said deodorized substrate with said enzyme in one or more tanks for a batch slurry reaction.

15. The method of claim 1, wherein said deodorized substrate is mixed with monohydroxyl alcohols or polyhydroxyl alcohols prior to contacting said deodorized substrate with said enzyme; and
wherein said esterified, transesterified or interesterified product is formed from the esterification, transesterification or interesterification of said monohydroxyl alcohols or polyhydroxyl alcohols.

16. The method of claim 15, wherein said monohydroxyl alcohols or said polyhydroxyl alcohols are primary, secondary or tertiary alcohols of annular, straight or branched chain compounds.

17. The method of claim 15, wherein said deodorized substrate is mixed with polyhydroxyl alcohols which are selected from the group consisting of glycerol, propylene glycol, ethylene glycol, 1,2-propanediol and 1,3-propanediol and combinations of any thereof.

18. The method of claim 1, wherein the deodorization holding time is from 5 minutes to 10 hours.

19. The method of claim 18, wherein the deodorization holding time is from 30 minutes to 3 hours.

20. The method of claim 1, wherein the deodorization stripping gas is steam, and the stripping steam ratio is 1-15 wt % of the initial substrate.

21. The method of claim 20, wherein the deodorization stripping gas is steam, and the stripping steam ratio is 1-5 wt % of the initial substrate.

22. The method of claim 1, further comprising preventing oxidative degradation of said initial substrate, said deodorized substrate, said esterified, transesterified or interesterified product or said enzyme.

23. The method of claim 9, wherein said initial substrate comprises partially or fully hydrogenated processed fats or oils, or fractionated fats or oils thereof, or combinations of any thereof.

24. The method of claim 1, further comprising contacting said initial substrate or said deodorized substrate with one or more types of purification media thereby producing a purification media-processed substrate.

25. The method of claim 24, wherein one or more of said initial substrate, said deodorized substrate, said purification media-processed substrate, said esterified, transesterified or interesterified product and said enzyme are in an inert gas environment.

26. The method of claim 25, wherein said inert gas is selected from the group consisting of $N_2$, $CO_2$, He, Ar, and Ne.

27. The method of claim 24, wherein said purification medium is selected from the group consisting of activated carbon, coal activated carbon, wood activated carbon, peat activated carbon, coconut shell activated carbon, natural minerals, processed minerals, montmorillonite, attapulgite, bentonite, palygorskite, Fuller's earth, diatomite, smectite, hormite, quartz sand, limestone, kaolin, ball clay, talc, pyrophyllite, perlite, silica, sodium silicate, silica hydrogel, silica gel, fumed silica, precipitated silica, dialytic silica, fibrous materials, cellulose, cellulose esters, cellulose ethers, microcrystalline cellulose; alumina, zeolite, starches, molecular sieves, previously used immobilized lipase, diatomaceous earth, ion exchange resin, size exclusion chromatography resin, chelating resins, chiral resins, rice hull ash, reverse phase silica, bleaching clays, and combinations of any thereof.

28. The method of claim 24, wherein said purification medium is silica having a surface area from 200 to 750 $m^2/g$, a mesh value from 3 to 425, an average particle size from 4-200 µ, an average pore radius from 20 to 150 Å, and an average pore volume from 0.68 to 1.15 $cm^3/g$.

29. The method of claim 28, wherein said silica is 35-60 mesh with an average pore size of about 60 Å.

30. The method of claim 24, wherein said one or more types of purification media and said enzyme are packed together or separately in one or more columns through which said initial substrate, said deodorized substrate, said purification media-processed substrate or said esterified, transesterified or interesterified product flows.

31. The method of claim 30, wherein said columns are jacketed columns, further comprising regulating the temperature of one or more of said initial substrate, said deodorized substrate, said purification media-processed substrate, said one or more types of purification media and said enzyme.

32. The method of claim 24, wherein said purification media-processed substrate is prepared by mixing said initial substrate or said deodorized substrate with said one or more types of purification media in a tank for a batch slurry purification reaction or mixing said initial substrate or said deodorized substrate in a series of tanks for a series of batch slurry purification reactions.

33. The method of claim 32, wherein said purification media-processed substrate is separated from said one or more types of purification media via filtration, centrifugation or concentration prior to reacting said purification media-processed substrate with said enzyme.

34. The method of claim 24, further comprising mixing said purification media-processed substrate with said enzyme in a tank for a batch slurry reaction, or flowing said purification media-processed substrate through a column containing said enzyme.

35. The method of claim 30, wherein a bed of said one or more types of purification media is placed upon a bed of said enzyme within a column.

36. The method of claim 25, further comprising preventing oxidative degradation to one or more of said initial substrate, said deodorized substrate, said purification media-processed substrate, said esterified, transesterified or interesterified product and said enzyme.

37. The method of claim 1, wherein said deodorized substrate has a peroxide value of less than 5 mEq/kg oil.

38. The method of claim 37, wherein said peroxide value is less than 2 mEq/kg oil.

39. The method of claim 38, wherein said peroxide value is less than 1 mEq/kg oil.

40. The method of claim 1, wherein said initial substrate is bleached, deodorized, refined, or a mixture thereof.

* * * * *